(12) United States Patent
Chen et al.

(10) Patent No.: US 6,180,401 B1
(45) Date of Patent: Jan. 30, 2001

(54) POLYPEPTIDE PRODUCTION IN ANIMAL CELL CULTURE

(75) Inventors: Mary Chen, Burlingame; Lawrence W. Forman, Sunnyvale, both of CA (US)

(73) Assignee: Genentech, Inc., South San Francisco, CA (US)

(*) Notice: Under 35 U.S.C. 154(b), the term of this patent shall be extended for 0 days.

(21) Appl. No.: 09/073,198

(22) Filed: May 4, 1998

Related U.S. Application Data

(62) Division of application No. 08/208,888, filed on Mar. 10, 1994, now Pat. No. 5,856,179.

(51) Int. Cl.$^7$ ............................... C12N 5/00; C12N 5/06

(52) U.S. Cl. ........................................... 435/358; 435/325

(58) Field of Search .................. 435/69.1, 69.7, 435/69.5, 69.6, 70.1, 70.3, 70.5, 325, 358, 360, 375

(56) References Cited

U.S. PATENT DOCUMENTS

| | | | |
|---|---|---|---|
| 3,926,723 | 12/1975 | Green et al. | 435/392 |
| 4,724,206 | 2/1988 | Rupp et al. | 435/68 |
| 5,122,469 | 6/1992 | Mather et al. | 435/383 |
| 5,151,359 | 9/1992 | Miyahara et al. | 435/226 |
| 5,284,763 | 2/1994 | Derynk et al. | 435/360 |
| 5,474,931 | 12/1995 | DiSorbo et al. | 435/407 |
| 5,856,179 | * 1/1999 | Chen et al. | 435/325 |

FOREIGN PATENT DOCUMENTS

| | | |
|---|---|---|
| 387840 | 9/1990 | (EP). |
| 481791 | 4/1992 | (EP). |
| 2251249 | 7/1992 | (GB). |
| 1-101882 | 4/1989 | (JP). |
| WO 87/00195 | 1/1987 | (WO). |
| WO 88/01643 | 3/1988 | (WO). |
| WO 89/04867 | 6/1989 | (WO). |

OTHER PUBLICATIONS

Kurano et al. (1990) Growth behavior of Chinese hamster ovary cells in a compact loop bioreactor. 2. Effects of medium components and waste products. Journal of Biotechnology 15: 113–128, Jul. 1990.*

Kurano et al. (1990) Growth behavior of Chinese hamster ovary cells in a compact loop bioreactor. 1. Effects of physical and chemical environment. Journal of Biotechnology 15: 101–112, Jul. 1990.*

GIBCO–BRL LIFE TECHNOLOGIES: 1993–1994 Catalogue and Reference Guide, pp. 1–16 to 1–24, 1993.*

Dircks et al., "High Glucose Concentrations Inhibit Protein Synthesis in Retinal Pigment Epithelium In Vitro" *Exp. Eye Res.* 44:951–958 (1987).

Fine et al., "Cell Culture Factors Influencing In Vitro Expression of Mouse Mammary Tumor Virus" *In Vitro* 12 (10) : 693–701 (1976).

Fleischaker, Jr., "An Experimental Study in the Use of Instrumentation to Analyze Metabolism and Product Formation in Cell Culture" *Massachusetts Institute of Technology* (Ph.D. Thesis) pps. 196–229 (1982)

Forman et al., "On–Line Monitoring and Control of Fermentation and Cell Culture Processes by Flow Injection Analysis" *Biosensors and Flow Injection Analysis in Bioprocess Control* (Oral Presentation), Freising, Germany (Apr. 8, 1992).

Garcia–Perez et al., "Molecular Cloning of cDNA Coding for Kidney Aldose Reductase" *Journal of Biological Chemistry* 264 (28) : 16815–16821 (1989).

Glacken et al., "Reduction of Waste Product Excretion via Nutrient Control: Possible Strategies for Maximizing Product and Cell Yields on Serum in Cultures of Mammalian Cells" *Biotechnol. Bioeng.* 28:1376–1389 (1986).

Graf et al., "Development of a continuous perfusion system for the cultivation of animal cells" *DECHEMA Biotechnol. Conf.* 3:615–618 (1989).

Hardjito et al., "Recombinant Protein Production via Fed–batch Culture of the Yeast Saccharomyces Cerevisiae" *Enzyme Micro. Technol.* 15:120–126 (1993).

Huang et al., "On–line determination pf glucose concentration throughout animal cell cultures based on chemiluminescent detection of hydrogen peroxide coupled with flow–injection analysis" *Journal Biotechnology* 18:161–162 (1991).

(List continued on next page.)

*Primary Examiner*—Einar Stole
(74) *Attorney, Agent, or Firm*—Skjerven Morrill MacPherson LLP; Emily M. Haliday

(57) ABSTRACT

A method of producing a polypeptide in fed batch cell culture is provided which involves an initial cell growth phase and a distinct production phase. In the initial growth stage, animal cells having nucleic acid encoding the polypeptide are cultured at a starting osmolality of about 280–330 mOsm in the presence of a concentration of glucose controlled throughout the culturing to be within a range between about 0.01 and 1 g/L. This is followed by a production phase, where the cultured animal cells of the growth phase are inoculated at a cell seed density of at least $1.0 \times 10^6$ cells/mL and the cells are cultured at a starting osmolarity of about 400–600 mOsm in the presence of a concentration of glucose controlled throughout the culturing to be within a range between about 0.01 and 1 g/L. Preferably, the glutamine concentration in the cell culture medium is simultaneously controlled in order to curtail production of lactic acid and ammonia which result from unnecessarily high glutamine concentrations. During the growth phase, production of potentially detrimental metabolic waste products, such as lactic acid, is controlled thereby curtailing the increase of osmolality due to accumulation and neutralization of waste products. Thus, the cell growth can be improved. In the production phase, the cell culture conditions are modified in order to arrest or reduce cell growth and thereby direct nutrient utilization toward production, as opposed to cell growth. Overall, it is intended that the method results in an improvement in specific productivity, reduction in production run times and/or an increase in final product concentration.

11 Claims, 3 Drawing Sheets

OTHER PUBLICATIONS

Iijima, "Effective Production of Biological Substances by High Cell Density Cultivation" *Journal of Society of Fermentation Engineering —Hakko Kogaku Kai Shi* (with English translation) 69(6) :507–520 (1991).

Loibner et al., "On–Line Glucose Control of Animal Cell Cultures in Fluidized Beds" *Biosensors and Flow Injection Analysis in Bioprocess Control* (Poster Presentation), Freising, Germany (Apr. 8, 1992).

Miner et al., "In vivo and in vitro Production and Detection of Monoclonal Antibodies to Surface Components on Metastatic Variants of Murine Tumor Cells" *Invasion Metastasis* 1:158–174 (1981).

Mizutani et al., "High Glucose and Hyperosmolarity Increase Platelet–derived Growth Factor mRNA Levels in Cultured Human Vascular Endothelial Cells" *Biochemical and Biophysical Research Communications* 187(2) :664–669 (1992).

Park et al., "Enhanced β—Galactosidase Production by High Cell–Density Culture of Recombinant Bacillus subtilis with Glucose Concentration Control" *Biotechnology and Bioengineering* 40:686–696 (1992).

Reuveny et al., "Factors affecting cell growth and monoclonal antibody production in stirred reactors" *Journal of Immunological Methods* 86:53–59 (1986).

Shak et al., "Recombinant Human DNase I Reduces the Viscosity of Cystic Fibrosis Sputum" *Proc. Natl. Acad. Sci. USA* 87(23) :9188–9192 (Dec. 1990).

Stubblefield et al., "Effects of Sodium Chloride Concentration on Growth, Biochemical Composition, and Metabolism of HeLa Cells" *Cancer Research* 20:1646–1655 (1960).

Sugiura, "Effects of Glucose on the Production of Recombinant Protein C in Mammalian Cells Culture" *Biotechnology and Bioengineering* 39:953–959 (1992).

Waymouth, "Osmolality of Mammalian Blood and of Media for Culture of Mammalian Cells" *In Vitro* 6(2): 109–127 (1970).

Werner et al., "Mammalian Cell Cultures, Part II: Genetic Engineering, Protein Glycosylation, Fermentation and Process Control" *Arzneim.—Forsch./Drug Res.* 43(11) : 1242–1249 (1993).

Xie and Wang, "Applications of Improved Stoichiometric Model in Medium Design and Fed–Batch Cultivation of Animal Cells in Bioreactor" *Cytotechnology* 15 :17–29 (1994).

* cited by examiner

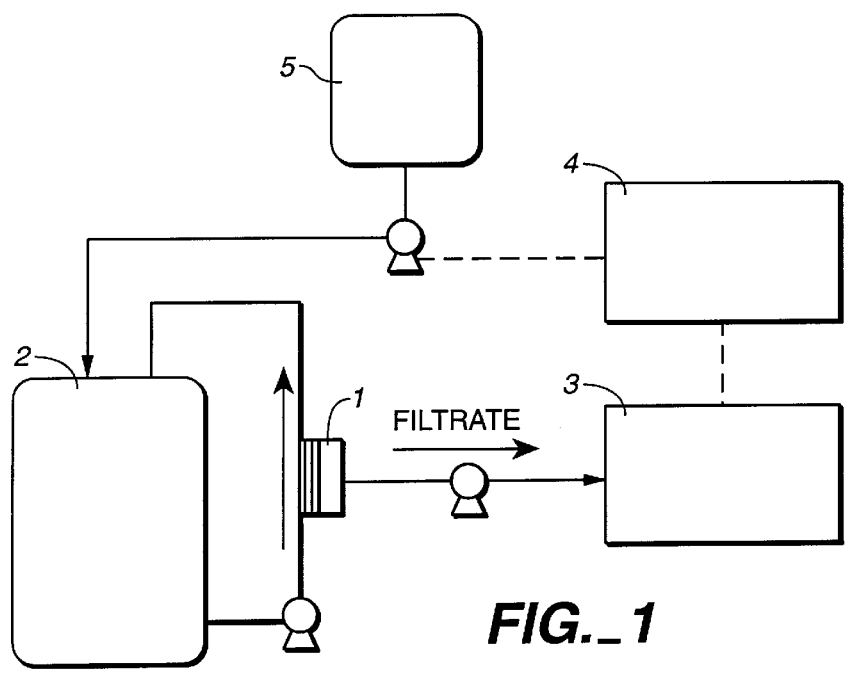
FIG._1
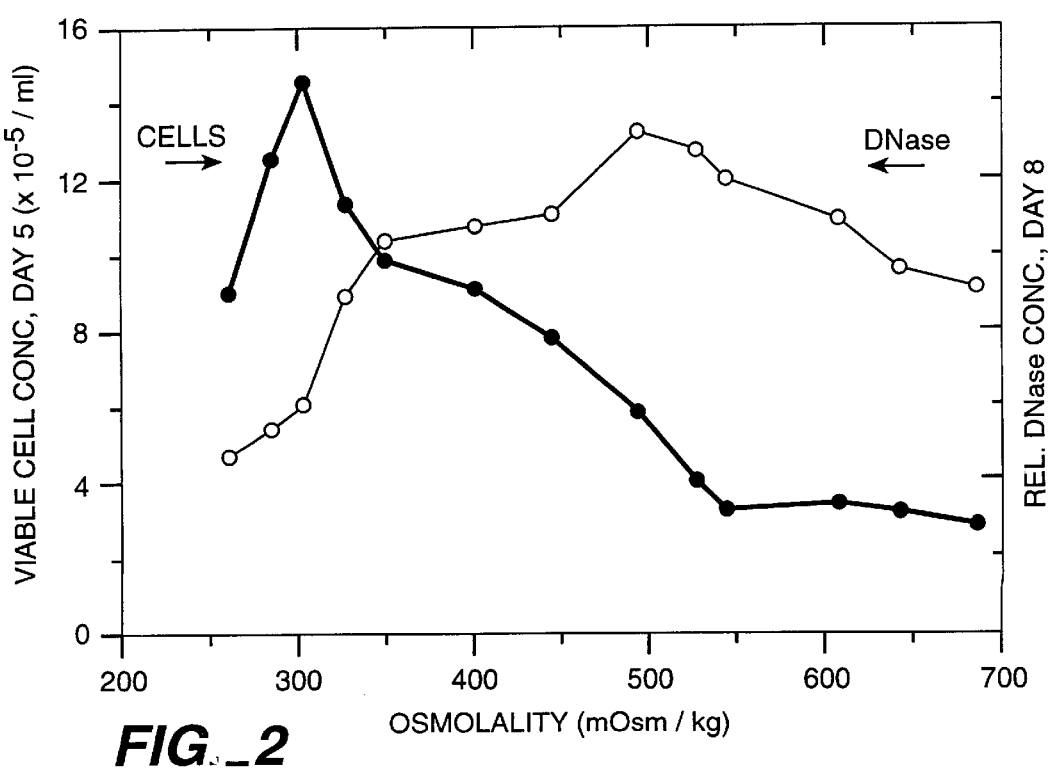
FIG._2

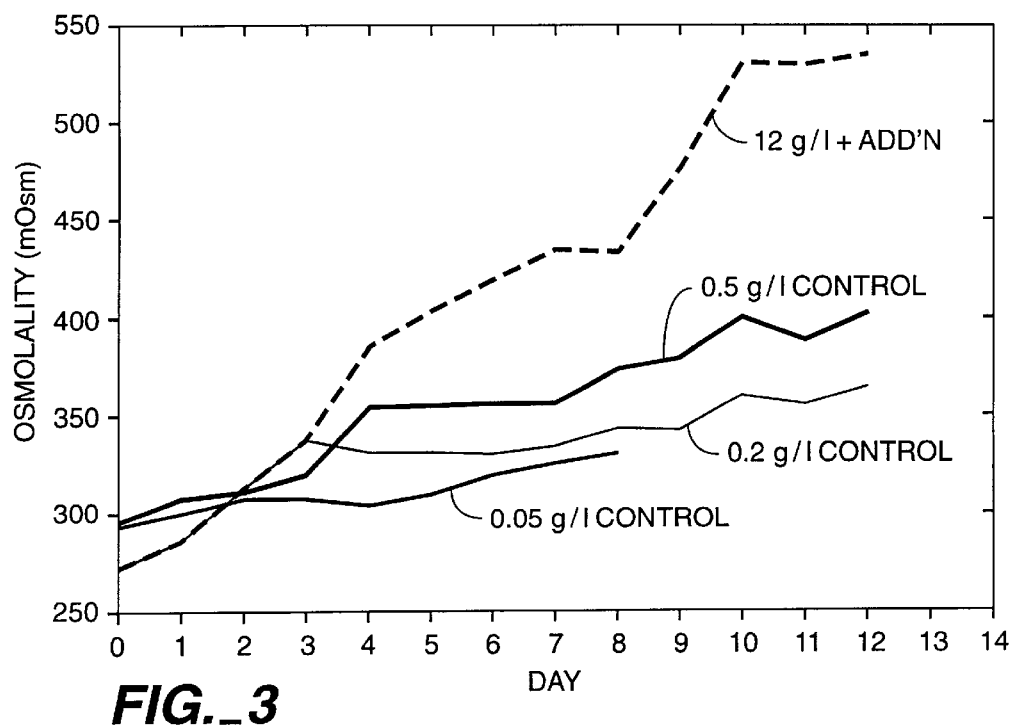
FIG._3
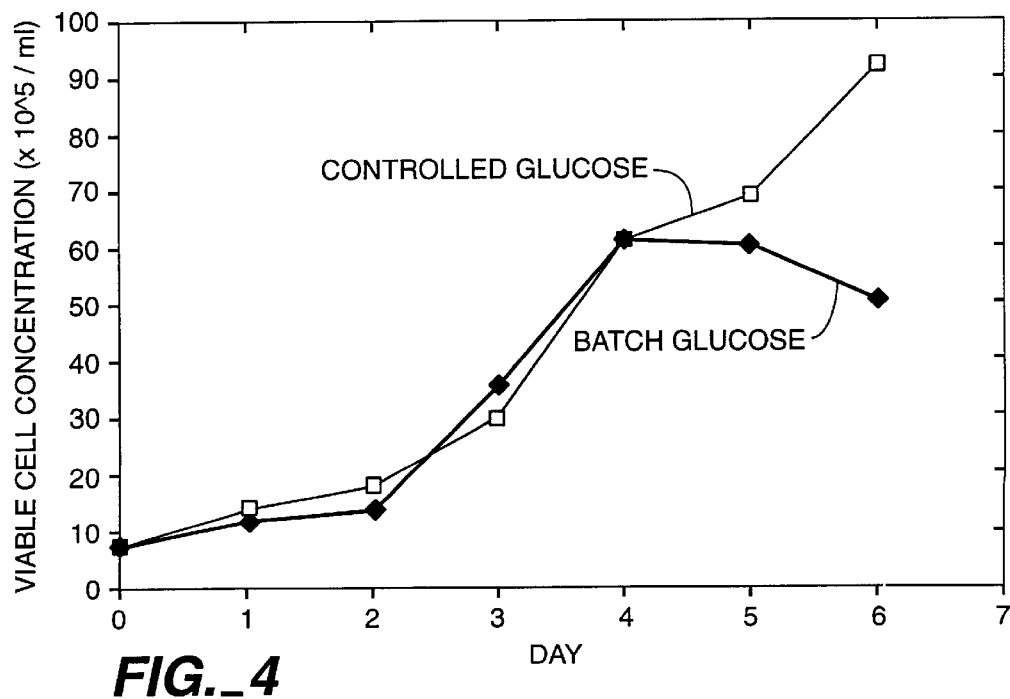
FIG._4

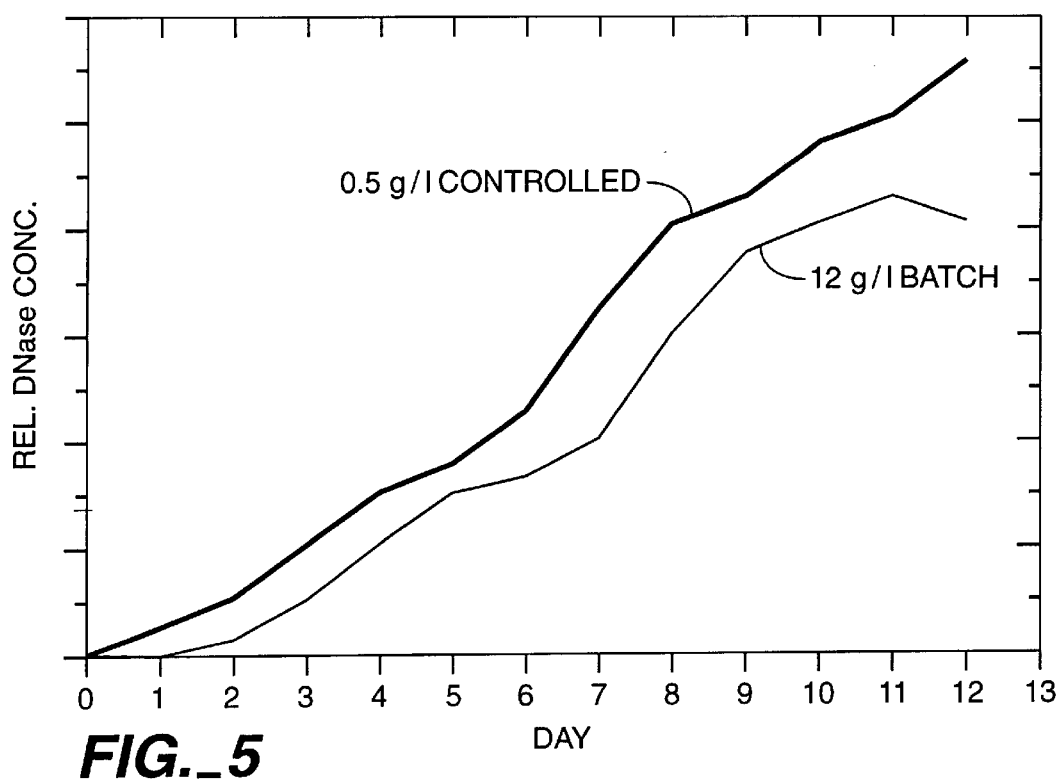
FIG._5
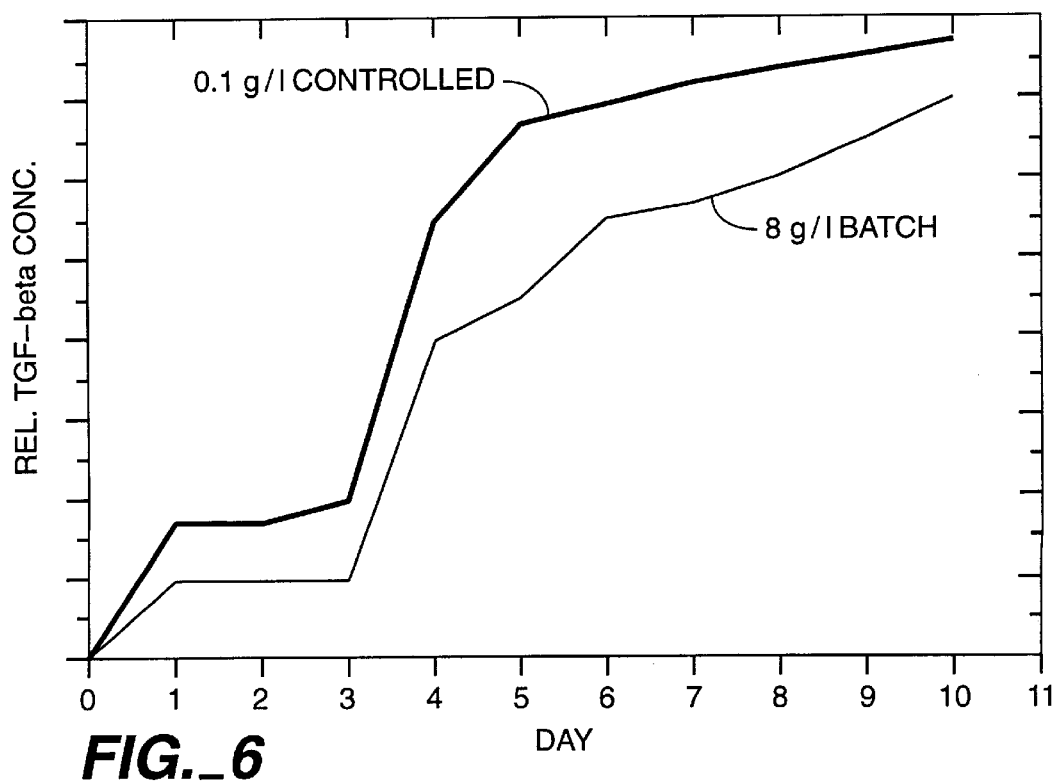
FIG._6

POLYPEPTIDE PRODUCTION IN ANIMAL CELL CULTURE

This is a divisional of application Ser. No. 08/208,888 filed on Mar. 10, 1994, now U.S. Pat. No. 5,856,179, which application is incorporated herein by reference and to which application priority is claimed under 35 USC §120.

BACKGROUND OF THE INVENTION

I. Field of the Invention

This invention relates to a method of improving polypeptide production in animal cell culture. In particular, it is directed to a method of culturing mammalian cells under conditions wherein the glucose concentration in the cell culture medium and the osmolality of the medium are controlled, so as to either promote cell growth or to promote recombinant polypeptide production.

II. Description of Related Art

With the advent of recombinant DNA technology the number of polypeptides which are able to be produced in recombinant cell culture has greatly increased. While some recombinant DNA techniques rely on bacterial or yeast cells for the production of polypeptides, production of polypeptides in animal cells (especially mammalian cells) is becoming widespread, particularly for the production of mammalian polypeptides. Similarly, cell fusion techniques for preparing hybridomas, which may be cultured to produce monoclonal antibodies (MAbs), are widely used.

Accordingly, techniques have been developed for enhancing cell growth and/or polypeptide production by such genetically modified animal cells. Several groups have looked at the effects of osmolality on cell growth and polypeptide production. See, for example, Stubblefield et al., Cancer Research, 20:1646–1655 (December 1960); Garcia-Perez et al., Journal of Biological Chemistry, 264(28):16815–16821 (1989); Miner et al., Invasion Metastasis, 1:158–174 (1981); GB 2,251,249; EP 481,791; U.S. Pat. No. 5,151,359; U.S. Pat. No. 4,724,206; U.S. Pat. No. 5,122,469; and WO 89/04867. Various osmolality ranges for cell growth or polypeptide production are recommended and, generally, the osmolality of the cell culture medium is increased via the addition of NaCl or amino acids. However, these publications fail to disclose a method of controlling the osmolality of the cell culture medium by controlling the addition of the primary energy source, glucose, to the cell culture medium.

Others have discussed the effect of glucose concentration on cell growth and/or polypeptide production in recombinant cell culture. See, for example, Park et al., Biotechnology and Bioengineering, 40:686–696 (1992); Huang et al., Journal of Biotechnology, 18:161–162 (1991); EP 387,840; Reuveny et al., Journal of Immunological Methods, 86:53–59 (1986); Fine et al., In Vitro, 12(10):693–701 (1976); Dircks et al., Exp. Eve Res., 44:951–958 (1987); Mizutani et al., Biochemical and Biophysical Research Communications, 187(2):664–669 (September 1992); Sugiura Biotechnology and Bioengineering, 39:953–959 (1992); WO 88/01643 Graf et al., DECHEMA Biotechnol. Conf., 3:615–618 (1989); Japanese Patent Appln No. JP 1-101882; U.S. Pat. No. 3,926,723; WO 87/00195; and Fleischaker, Jr., Ph.D. Thesis, Massachusetts Institute of Technology, pp. 196–229 (June 1982).

Glacken et al., Biotechnol. Bioeng., 28: 1376–1389 (1986) have also studied the effect of glutamine on cell cultures.

However, the concept of controlling glucose in fed-batch cell culture in order to control osmolality within a desired range has not been proposed by these researchers.

Accordingly, it is an object of the present invention to provide a method of controlling fed batch cell culture conditions for growth of animal cells so as to maintain high cell viability or extend the period of rapid cell growth. It is a further object to control production of potentially detrimental metabolic waste products, such as lactic acid, during culturing of mammalian cells. Also, it is an object to curtail the increase of osmolality, due to accumulation and neutralization of waste products and subsequent replacement of consumed glucose. Thus, cell viability can be improved by controlling the osmolality and production of waste products.

It is another object of the invention to provide a method of manipulating fed batch cell culture conditions to increase production of a polypeptide by animal cells which have nucleic acid encoding the polypeptide. In the production phase, the cell culture conditions are modified in order to arrest or curtail cell growth and thereby direct nutrient utilization toward production, as opposed to cell replication. Overall, it is intended that the method results in an improvement in specific productivity, reduction in production run times and/or an increase in final product concentration.

It is a further object of the present invention to provide a method of making a polypeptide which comprises initially culturing animal cells under conditions which enhance cell growth and then, in a production phase distinct from the cell growth phase, culturing animal cells under conditions which increase protein production thereby. This enables the growth phase of the production culture to be reduced or eliminated, thereby resulting in a concomitant decrease in the time required for optimal production of the polypeptide of interest by the cell culture. This is particularly desirable for products such as DNase which tend to undergo deamidation in cell culture over protracted periods.

It is a further object of the invention to control the osmolality of an animal cell culture to be substantially maintained within a desired range, via control of the glucose and, optionally, glutamine concentration in the culture medium. This is particularly desirable insofar as the optimal osmolalities for animal cell growth and polypeptide production by animal cells have been identified herein.

Other objects and advantages of the present invention will become apparent to one of ordinary skill in the art.

SUMMARY OF THE INVENTION

In accordance with the objects of the invention, a method of growing animal cells in fed batch cell culture is provided which comprises the steps of culturing the cells at a starting osmolality of about 280–330 mOsm and controlling the glucose concentration in the cell culture to be between about 0.01 and 1 g/L throughout the culturing.

In another aspect, the invention relates to a method of producing a polypeptide by animal cells which contain nucleic acid encoding the polypeptide in fed batch cell culture, wherein the starting osmolality of the cell culture is about 400–600 mOsm and the glucose concentration in the cell culture is controlled to be between about 0.01 and 1 g/L throughout the culturing. The starting cell density of the cell culture is at least about $1.0 \times 10^6$ cells/mL, preferably at least about $3.0 \times 10^6$ cells/mL.

In yet a further aspect, a method of producing a polypeptide in fed batch cell culture is provided which involves an initial cell growth phase and a distinct production phase. In the initial growth phase, animal cells having nucleic acid encoding the polypeptide are cultured at a starting osmolarity of about 280–330 mOsm in the presence of a concentration of glucose controlled throughout the culturing to be within a range between about 0.01 and 1 g/L. This is followed by a production phase, where the cultured animal cells of the growth phase are inoculated at a cell seed density of at least about $1.0 \times 10^6$ cells/mL and the cells are cultured at a starting osmolality of about 400–600 mOsm in the presence of a concentration of glucose controlled throughout the culturing to be within a range between about 0.01 and 1 g/L.

Preferably, the glutamine concentration in the cell culture medium is simultaneously controlled in order to control production of lactic acid and ammonia, which results from unnecessarily high glutamine concentrations.

In the preferred embodiment, the cells are mammalian cells, such as chinese hamster ovary (CHO) cells and the polypeptide is DNase or TGF-β.

BRIEF DESCRIPTION OF THE DRAWINGS

FIG. 1 is a schematic diagram of a glucose control system suitable for practicing the instant invention;

FIG. 2 depicts the impact of osmolality on DNase expression and growth of CHO cells;

FIG. 3 depicts the osmolality change during cultivation at various controlled glucose concentrations versus high (batch) glucose concentration;

FIG. 4 depicts cell growth over time at controlled (low) glucose concentration versus high (batch) glucose concentration;

FIG. 5 depicts DNase production at controlled (low) glucose concentration versus high (batch) glucose concentration; and FIG. 6 depicts TGFβ production in controlled (low) glucose concentration versus high (batch) glucose concentration.

DETAILED DESCRIPTION OF THE PREFERRED EMBODIMENTS DEFINITIONS

The phrase "fed batch cell culture" when used herein refers to a batch culture wherein the animal cells and culture medium are supplied to the culturing vessel initially and additional culture nutrients are fed, continuously or in discrete increments, to the culture during culturing, with or without periodic cell and/or product harvest before termination of culture. Fed batch culture includes "semi-continuous fed batch culture" wherein periodically whole culture (including cells and medium) is removed and replaced by fresh medium. Fed batch culture is distinguished from simple "batch culture" in which all components for cell culturing (including the animal cells and all culture nutrients) are supplied to the culturing vessel at the start of the culturing process. Fed batch culture can be further distinguished from perfusion culturing insofar as the supernate is not removed from the culturing vessel during the process (in perfusion culturing, the cells are restrained in the culture by, e.g., filtration, encapsulation, anchoring to microcarriers etc and the culture medium is continuously or intermittently introduced and removed from the culturing vessel). However, removal of samples for testing purposes during fed batch cell culture is contemplated.

The term "animal cells" encompasses invertebrate, non-mammalian vertebrate (e.g., avian, reptile and amphibian) and mammalian cells. Examples of invertebrate cells include the following insect cells: *Spodoptera frugiperda* (caterpillar), *Aedes aegypti* (mosquito), *Aedes albopictus* (mosquito), *Drosophila melanogaster* (fruitfly), and *Bombyx mori*. See, e.g., Luckow et al., *Bio/Technology*, 6:47–55 (1988); Miller et al., in *Genetic Engineering*, Setlow, J. K. et al., eds., Vol. 8 (Plenum Publishing, 1986), pp. 277–279; and Maeda et al., *Nature*, 315:592–594 (1985).

In preferred embodiments, the cells are mammalian cells. Examples of mammalian cells include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 [1977]); baby hamster kidney cells (BHK, ATCC CCL 10); Chinese hamster ovary cells/-DHFR (CHO, Urlaub and Chasin, *Proc. Natl. Acad. Sci. USA*, 77:4216 [1980]); mouse sertoli cells (TM4, Mather, *Biol. Reprod.*, 23:243–251 [1980]); monkey kidney cells (CV1 ATCC CCL 70); African green monkey kidney cells (VERO-76, ATCC CRL-1587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.*, 383:44–68 [1982]); MRC 5 cells; FS4 cells; and a human hepatoma line (Hep G2). CHO cells are the preferred cell line for practicing the invention.

The invention is also applicable to hybridoma cells. The term "hybridoma" refers to a hybrid cell line produced by the fusion of an immortal cell line of immunologic origin and an antibody producing cell. The term encompasses progeny of heterohybrid myeloma fusions, which are the result of a fusion with human cells and a murine myeloma cell line subsequently fused with a plasma cell, commonly known as a trioma cell line. Furthermore, the term is meant to include any immortalized hybrid cell line which produces antibodies such as, for example, quadromas. See, e.g., Milstein et al., *Nature*, 537:3053 (1983). The hybrid cell lines can be of any species, including human and mouse.

In the most preferred embodiment however, the mammalian cell is a non-hybridoma mammalian cell which has been transformed with exogenous nucleic acid encoding a polypeptide of interest. By "exogenous nucleic acid" is meant a nucleic acid sequence that is foreign to the cell, or homologous to the cell but in a position within the host cell nucleic acid in which the nucleic acid is ordinarily not found.

The expression "osmolality" is a measure of the osmotic pressure of dissolved solute particles in an aqueous solution. The solute particles include both ions and non-ionized molecules. osmolality is expressed as the concentration of osmotically active particles (i.e., osmoles) dissolved in 1 kg of water (1 mOsm/kg $H_2O$ at 38° C. is equivalent to an osmotic pressure of 19 mm Hg). "Osmolarity" refers to the number of solute particles dissolved in 1 liter of solution. Solutes which can be added to the culture medium so as to increase the osmolality thereof include proteins, peptides, amino acids, non-metabolized polymers, vitamins, ions, salts, sugars, metabolites, organic acids, lipids, etc. In the preferred embodiment, the concentration of amino acids and NaCl in the culture medium is increased in order to achieve the desired osmolality ranges set forth herein. When used herein, the abbreviation "mOsm" means "milliosmoles/kg $H_2O$".

The word "glucose" refers to either of α-D-glucose or β-D-glucose, separately or in combination. It is noted that α and β glucose forms are interconvertible in solution.

When used herein, the term "glutamine" refers to the amino acid L-glutamine (also known as "Gln" and "Q" by three-letter and single-letter designation, respectively)

which is recognized as both an amino acid building block for protein synthesis and as an energy source in cell culture.

The terms "amino acids" and "amino acid" refer to all naturally occurring alpha amino acids in both their D and L stereoisomeric forms, and their analogs and derivatives. An analog is defined as a substitution of an atom in the amino acid with a different atom that usually has similar properties. A derivative is defined as an amino acid that has another molecule or atom attached to it. Derivatives would include, for example, acetylation of an amino group, amination of a carboxyl group, or oxidation of the sulfur residues of two cysteine molecules to form cystine.

As used herein, "polypeptide of interest" refers generally to peptides and proteins having more than about ten amino acids. The polypeptides may be homologous to the host cell, or preferably, may be exogenous, meaning that they are heterologous, i.e., foreign, to the host cell being utilized, such as a human protein produced by a Chinese hamster ovary cell, or a yeast polypeptide produced by a mammalian cell. Preferably, mammalian polypeptides (polypeptides that were originally derived from a mammalian organism) are used, more preferably those which are directly secreted into the medium.

Examples of bacterial polypeptides include, e.g., alkaline phosphatase and β-lactamase. Examples of mammalian polypeptides include molecules such as renin, a growth hormone, including human growth hormone; bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressing; regulatory proteins; antibodies; and fragments of any of the above-listed polypeptides.

The most preferred polypeptides of interest are human polypeptides such as deoxyribonuclease (DNase) and transforming growth factor-β (TGFβ).

The terms "cell culture medium" and "culture medium" refer to a nutrient solution used for growing mammalian cells that typically provides at least one component from one or more of the following categories:

1) an energy source, usually in the form of a carbohydrate such as glucose;
2) all essential amino acids, and usually the basic set of twenty amino acids plus cystine;
3) vitamins and/or other organic compounds required at low concentrations;
4) free fatty acids; and
5) trace elements, where trace elements are defined as inorganic compounds or naturally occurring elements that are typically required at very low concentrations, usually in the micromolar range.

The nutrient solution may optionally be supplemented with one or more components from any of the following categories:

1) hormones and other growth factors as, for example, insulin, transferrin, and epidermal growth factor;
2) salts and buffers as, for example, calcium, magnesium, and phosphate;
3) nucleosides and bases such as, for example, adenosine and thymidine, hypoxanthine; and
4) protein and tissue hydrolysates.

Modes for Practicing the Invention

1. Growth Phase

In a first aspect, the invention relates to a growth phase wherein fed batch cell culture conditions are modified to enhance growth of recombinant animal cells. In the growth phase, the basal culture medium and animal cells are supplied to the culturing vessel in batch. In the preferred embodiment of the invention the cell culture medium comprises excess amino acids. The amino acids which are provided in excess may, for example, be selected from Asn, Asp, Gly, Ile, Leu, Lys, Met, Ser, Thr, Trp, Tyr and Val. Preferably, Asn, Asp, Lys, Met, Ser and Trp are provided in excess. For example, amino acid concentrations in the ranges specified below in Table 1 may be used:

TABLE 1

| Amino Acid | Suitable Concentration (mg/l) | Preferred Concentration (mg/l) |
|---|---|---|
| Asn | 150–450 | 200–300 |
| Asp | 150–450 | 200–300 |
| Lys | 400–800 | 550–650 |
| Met | 50–200 | 50–100 |
| Ser | 100–300 | 100–200 |
| Trp | 50–200 | 50–100 |

The most preferred concentration for each of the amino acids is as follows: Asn at 262 mg/l; Asp at 232 mg/l; Lys at 602 mg/l; Met at 61 mg/l; Ser at 173 mg/l; and Trp at 75 mg/l.

Alternatively, the amino acid concentrations shown in Table 1 of U.S. Pat. No. 5,122,469 (the disclosure of which is incorporated herein by reference) can be present in the culture medium.

For convenience, each amino acid can be weighed out in a predetermined amount; the amino acids can then be combined together and stored as the amino acid supplement mixture.

The medium used to practice this invention may be any mammalian cell culture medium, but preferably the naturally occurring twenty amino acids and cystine are present at about the molar ratios listed in Table 2.

TABLE 2

| Amino Acid | Molar Ratio to Tryptophan |
|---|---|
| Alanine | 4.72 |
| Arginine, monohydrochloride | 49.99 |
| Asparagine, monohydrate | 4.72 |
| Aspartic Acid | 4.72 |
| Cysteine, monohydrochloride, monohydrate | 9.45 |
| Cystine, dihydrochloride | 1.35 |
| Glutamic Acid | 4.71 |
| Glutamine | 148.35 |
| Glycine | 7.42 |
| Histidine, monohydrochloride, monohydrate | 6.08 |
| Isoleucine | 6.82 |
| Leucine | 10.12 |
| Lysine, monohydrochloride | 14.83 |
| Methionine | 2.77 |
| Phenylalanine | 4.11 |
| Proline | 14.18 |
| Serine | 7.42 |
| Threonine | 10.10 |
| Tryptophan | 1.00 |
| Tyrosine, disodium salt, dihydrate | 4.06 |
| Valine | 10.13 |

One appropriate cell culture medium that may be supplemented with amino acids at elevated levels is the medium termed "PS-04". The components of this medium are listed in Table 3 below.

TABLE 3

| Component | Concentration (mg/l) |
|---|---|
| Calcium chloride, anhydrous | 116.61 |
| Cupric sulfate, pentahydrate | 0.0012 |
| Ferric nitrate, nonahydrate | 0.05 |
| Ferrous sulfate, heptahydrate | 0.417 |
| Potassium chloride | 759.0 |
| Magnesium sulfate, anhydrous | 48.835 |
| Magnesium chloride, anhydrous | 143.05 |
| Sodium phosphate, monobasic, monohydrate | 62.5 |
| Sodium phosphate, dibasic, anhydrous | 71.02 |
| Zinc sulfate, heptahydrate | 0.4315 |
| Hypoxanthine | 16.695 |
| Linoleic acid | 0.294 |
| Lipoic acid | 0.735 |
| Putrescine, dihydrochloride | 0.5635 |
| Sodium pyruvate | 385.0 |
| Thymidine | 2.555 |
| Alanine | 31.15 |
| Arginine, monohydrochloride | 780.5 |
| Asparagine, monohydrate | 52.53 |
| Aspartic acid | 46.55 |
| Cysteine, monohydrochloride, monohydrate | 122.92 |
| Cystine, dihydrochloride | 31.285 |
| Glutamic acid | 51.45 |
| Glutamine | 1606.0 |
| Glycine | 41.25 |
| Histidine, monohydrochloride, monohydrate | 94.36 |
| Isoleucine | 66.29 |
| Leucine | 98.35 |
| Lysine, monohydrochloride | 200.75 |
| Methionine | 30.68 |
| Phenylalanine | 50.36 |
| Proline | 120.75 |
| Serine | 57.75 |
| Threonine | 89.15 |
| Tryptophan | 15.14 |
| Tyrosine, disodium salt, dihydrate | 79.125 |
| Valine | 87.95 |
| Biotin | 0.0256 |

TABLE 3-continued

| Component | Concentration (mg/l) |
|---|---|
| D-Calcium pantothenate | 3.68 |
| Choline chloride | 50.86 |
| Cyanocobalamin | 4.76 |
| Folic acid | 6.55 |
| i-Inositol | 66.60 |
| Nicotinamide | 2.1295 |
| Pyridoxal, monohydrochloride | 2.000 |
| Pyridoxine, monohydrochloride | 0.217 |
| Riboflavin | 0.3330 |
| Thiamine, monohydrochloride | 3.190 |
| Glucose | 4300.0 |
| Sodium bicarbonate | 1220.0 |
| Sodium chloride | 7360.0 |
| Pluronic F-68 Prill | 1000.0 |
| Gentamycin sulfate | 100.0 |

For convenience, the solid ingredients of the medium may be combined together with the amino acids, and this mixture may be stored as a single unit.

One preferred medium of this invention that contains the selected amino acids at the elevated levels is the medium called "Diesel". The ingredients and the preferred concentrations are is listed below in Table 4.

TABLE 4

| Component | Concentration (mg/l) |
|---|---|
| Calcium chloride, anhydrous | 116.61 |
| Cupric sulfate, pentahydrate | 0.0012 |
| Ferric nitrate, nonahydrate | 0.05 |
| Ferrous sulfate, heptahydrate | 0.417 |
| Potassium chloride | 759.0 |
| Magnesium sulfate, anhydrous | 48.835 |
| Magnesium chloride, anhydrous | 143.05 |
| Sodium phosphate, monobasic, monohydrate | 62.5 |
| Sodium phosphate, dibasic, anhydrous | 71.02 |
| Zinc sulfate, heptahydrate | 0.4315 |
| Hypoxanthine | 16.695 |
| Linoleic acid | 0.294 |
| Lipoic acid | 0.735 |
| Putrescine, dihydrochloride | 0.5635 |
| Sodium pyruvate | 385.0 |
| Thymidine | 2.555 |
| Alanine | 31.15 |
| Arginine, monohydrochloride | 780.5 |
| Asparagine, monohydrate | 262.69 |
| Aspartic acid | 232.75 |
| Cysteine, monohydrochloride, monohydrate | 122.92 |
| Cystine, dihydrochloride | 31.285 |
| Glutamic acid | 51.45 |
| Glutamine | 1606.0 |
| Glycine | 41.25 |
| Histidine, monohydrochloride, monohydrate | 94.36 |
| Isoleucine | 66.29 |
| Leucine | 98.35 |
| Lysine, monohydrochloride | 602.25 |
| Methionine | 61.36 |
| Phenylalanine | 50.36 |
| Proline | 120.75 |
| Serine | 173.25 |
| Threonine | 89.15 |
| Tryptophan | 15.14 |
| Tyrosine, disodium salt, dihydrate | 79.125 |
| Valine | 87.95 |
| Biotin | 0.0256 |
| D-Calcium pantothenate | 3.68 |
| Choline chloride | 50.86 |
| Cyanocobalamin | 4.76 |
| Folic acid | 6.55 |
| i-Inositol | 66.60 |
| Nicotinamide | 2.1295 |
| Pyridoxal, monohydrochloride | 2.000 |
| Pyridoxine, monohydrochloride | 0.217 |

TABLE 4-continued

| Component | Concentration (mg/l) |
|---|---|
| Riboflavin | 0.3330 |
| Thiamine, monohydrochloride | 3.190 |
| Glucose | 4300.0 |
| Sodium bicarbonate | 1220.0 |
| Sodium chloride | 7360.0 |
| Pluronic F-68 Prill | 1000.0 |
| Gentamycin sulfate | 100.0 |

Alternatively, commercially available media such as Ham's F10 (Sigma), Minimal Essential Medium ([MEM], Sigma), RPMI-1640 (Sigma), and Dulbecco's Modified Eagle's Medium ([DMEM], Sigma) are suitable for culturing the animal cells. In addition, any of the media described in Ham and Wallace, *Meth. Enz.*, 58:44 (1979), Barnes and Sato, *Anal. Biochem.*, 102:255 (1980), U.S. Pat. Nos. 4,767,704; 4,657,866; 4,927,762; or 4,560,655; WO 90/03430; WO 87/00195; U.S. Pat. No. Re. 30,985; or U.S. Pat. No. 5,122,469, the disclosures of all of which are incorporated herein by reference, may be used as culture media for the host cells. Any of these media may be supplemented as necessary with hormones and/or other growth factors (such as insulin, transferrin, or epidermal growth factor), ions (such as sodium, chloride, calcium, magnesium, and phosphate), buffers (such as HEPES), nucleosides (such as adenosine and thymidine), trace elements (defined as inorganic compounds usually present at final concentrations in the micromolar range), and glucose or an equivalent energy source. Any other necessary supplements may also be included at appropriate concentrations that would be known to those skilled in the art.

The initial osmolality of the culture medium is in the range of about 280–330 mOsm. The osmolality can be measured using an osmometer such as that sold by Fischer Scientific, Pittsburg, Pa., under the brand name OSMETTE™, for example. In order to achieve an osmolality in this range, the concentration of various constituents in the culture medium can be adjusted. In the preferred embodiment, the culture medium contains excess amino acids (see, e.g., the "Super" medium of U.S. Pat. No. 5,122,469) and the osmolality is adjusted to 280–330 mOsm via the addition of a basal concentration of glucose (in the concentration specified herein) and, optionally, a salt (e.g., NaCl). It will be appreciated however, that the concentration (s) of other constituents in the culture medium can be modified in order to achieve an osmolality range as set forth above.

The culturing vessel is inoculated with the animal cells. A suitable initial cell seed density for the cell growth phase is in the range $3 \times 10^5$ to $1.5 \times 10^6$ cells/ml, for example. A suitable culturing vessel for cell growth is a pH controlled bioreactor. An autoclavable glass fermenter (sold by Applikon, Foster City, Calif.) or stainless steel fermenter (sold by Biolafitte, Princeton, N.J.) are available for use with the invention. Other culturing vessels suitable for practicing the invention are well known in the art.

FIG. 1 shows a culturing system which is suitable for practicing the invention set forth herein. The main system components are a tangential flow filtration sample device (1) contained within a recycle loop which is aseptically attached to the culturing vessel or bioreactor (2), an analyzer (3) e.g., a flow injection analyzer (FIA) which determines the glucose concentration of a cell-free medium sample provided by the sample device, a process computer or controller (4) capable of turning a glucose feed pump on or off to maintain the desired concentration, and a feed tank (5) containing sterile concentrated glucose solution which is pumped, as required, into the bioreactor (2).

As mentioned above, the starting osmolality of the culture medium is about 280–330 mOsm and is preferably maintained at a low concentration near the range of about 280–330 mOsm throughout the culturing. Conveniently, it has been found that by controlling the concentration of glucose (the primary energy source) in the culture medium throughout the culturing, the osmolality of the medium can be maintained at about the desirable range specified. Controlling the glucose concentration serves to provide adequate carbon source to the cells and simultaneously control the production of lactic acid by the host cells. This is advantageous in that it limits the pH decrease in the culture medium which necessitates the addition of a neutralizer (e.g., a base such as $Na_2CO_3$ or NaOH), which causes the osmolality to rise. It has been found that such increases in osmolality have a negative effect on cell growth or viability in the culture medium.

In the experiments herein disclosed, it has been found that a suitable overall glucose concentration for the culture medium is in the range 0.01–1 g/L, preferably 0.02–0.5 g/L, and more preferably 0.05–0.2 g/L. In order to monitor and maintain the glucose concentration within the desired range, flow injection analysis (i.e., FIA, disclosed in Huang et al., supra, or Ruzicka and Hanson, in *Flow Injection Analysis*, 1988, 2nd Ed., John Wiley & Sons, New York, for example) provides a convenient mechanism for on-line monitoring and control of glucose concentration. In an exemplary FIA system, a small quantity of filtered process medium (about 7 $\mu$l) is introduced into a flowing carrier stream (phosphate buffered saline solution, modified by addition of antimicrobial agents and by addition of NaCl to bring its osmolality to a value near the middle of the expected process osmolality range) by a HPLC-type injection valve. The sample is diluted about 70-fold as it passes through a diluter on its way to the flow-through detector. Detection is accomplished using an electrochemical electrode covered by a membrane containing immobilized glucose oxidase (Yellow Springs Instrument Co., Yellow Springs, Ohio). The signal from the electrode/conditioner is transmitted to the process controller or computer where process signals are compared with stored values obtained with standard glucose solutions; the appropriate signal (on or off) is transmitted to the glucose feed pump. FIA is desirable insofar as it provides a system for the real-time measurement and control of glucose concentration in mammalian cell cultures with the potential for frequent sampling and automated sample pretreatment.

Alternatively, intermittent off-line sampling of the culture medium can be carried out. The glucose concentration of the culture medium can then be modified by the modulation of a glucose feed solution as required.

In at least one embodiment of the invention, the glutamine concentration in the culture medium is controlled simultaneously with the glucose concentration. Such control is desirable because glutamine is utilized more rapidly by mammalian cells at low glucose concentrations and this leads to the production of waste products such as ammonia and lactic acid which can have direct negative effects on cell growth and/or production and tend to cause the osmolality to increase. Preferably, the glutamine concentration is controlled throughout the culturing to be in a range of 0.2 to 2 mM, more preferably 0.5 to 1 mM. Control of the glutamine concentration can be achieved using ;a FIA system discussed above, for example.

The culture conditions, such as temperature, pH, dissolved oxygen ($dO_2$) and the like, are those previously used with the host cell selected for cell growth, and will be apparent to the ordinarily skilled artisan. Generally, the pH is adjusted to a level between about 6.5 and 7.5 using either an acid (e.g., $CO_2$) or a base (e.g., $Na_2CO_3$ or NaOH). A suitable temperature range for culturing mammalian cells such as CHO cells is between about 30 to 38° C. and a suitable $dO_2$ is between 5–90%.

While the cells of the growth phase need not be transformed with exogenous nucleic acid, in the preferred embodiment of the invention, the cell growth phase is followed by a distinct polypeptide production phase wherein the cells have been transformed with exogenous nucleic acid encoding the polypeptide of interest. Suitable methods for transformation of the animal cells follow.

2. Transformation of Animal Cells

In order to isolate the nucleic acid encoding the polypeptide of interest, libraries are screened with probes designed to identify the gene encoding the polypeptide or the polypeptide per se. For cDNA expression libraries, suitable probes include monoclonal or polyclonal antibodies that recognize and specifically bind to the polypeptide of interest; oligonucleotides of about 20–80 bases in length that encode known or suspected portions of the polypeptide's cDNA from the same or different species; and/or complementary or homologous cDNAs or fragments thereof that encode the same or a similar gene. Appropriate probes for screening genomic DNA libraries include, but are not limited to, oligonucleotides, cDNAs, or fragments thereof that encode the same or a similar gene, and/or homologous genomic DNAs or fragments thereof. Screening the cDNA or genomic library with the selected probe may be conducted using standard procedures as described in chapters 10–12 of Sambrook et al., *Molecular Cloning: A Laboratory Manual* (New York: Cold Spring Harbor Laboratory Press, 1989).

The nucleic acid (e.g., cDNA or genomic DNA) encoding the polypeptide of interest is inserted into a replicable vector for further cloning (amplification of the DNA) or for expression. Many vectors are available. Each vector contains various components depending on its function (amplification of DNA or expression of DNA) and the host cell with which it is compatible. The vector components generally include, but are not limited to, one or more of the following: a signal sequence, one or more marker genes, an enhancer element, a promoter, and a transcription termination sequence.

The native signal sequence (i.e., the presequence that normally directs secretion of the polypeptide of interest) is satisfactory, although other mammalian signal sequences may be suitable, such as signal sequences from other animal polypeptides, and signal sequences from secreted polypeptides of the same or related species, as well as viral secretory leaders, for example, the herpes simplex gD signal. The DNA for such precursor region is ligated in reading frame to DNA encoding the mature polypeptide.

Suitable selectable markers for mammalian cells are those that enable the identification of cells competent to take up the nucleic acid from the polypeptide, such as DHFR or thymidine kinase. The mammalian cell transformants are placed under selection pressure that only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes the polypeptide of interest. Amplification is the process by which genes in greater demand for the production of a protein critical for growth are reiterated in tandem within the chromosomes of successive generations of recombinant cells. Increased quantities of the polypeptide are synthesized from the amplified DNA. Other examples of amplifiable genes include metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin, *Proc. Natl. Acad. Sci. USA,* 77:4216 (1980). The transformed cells are then exposed to increased levels of methotrexate. This leads to the synthesis of multiple copies of the DHFR gene, and, concomitantly, multiple copies of other DNA comprising the expression vectors, such as the DNA encoding the polypeptide of interest. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060).

Polypeptide transcription from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, and from the promoter normally associated with the polypeptide sequence, provided such promoters are compatible with the host cell systems.

The early and late promoters of the SV40 virus are conveniently obtained as an SV40 restriction fragment that also contains the SV40 viral origin of replication. Fiers et al., *Nature,* 273:113 (1978); Mulligan and Berg, *Science,* 209:1422–1427 (1980); Pavlakis et al., *Proc. Natl. Acad. Sci. USA,* 78:7398–7402 (1981). The immediate early promoter of the human cytomegalovirus is conveniently obtained as a HindIII E restriction fragment. Greenaway et al., *Gene,* 18:355–360 (1982). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., *Nature,* 295:503–508 (1982) on expressing cDNA encoding immune interferon in monkey cells; Reyes et al., *Nature,* 297:598–601 (1982) on expression of human β-interferon cDNA in mouse cells under the control of a thymidine kinase promoter from herpes simplex virus; Canaani and Berg, *Proc. Natl. Acad. Sci. USA,* 79:5166–5170 (1982) on expression of the human interferon β1 gene in cultured mouse and rabbit cells; and Gorman et al., *Proc. Natl. Acad. Sci. USA,* 79:6777–6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

Transcription of a DNA encoding the polypeptide of interest by higher eukaryotes is often increased by inserting an enhancer sequence into the vector. Enhancers are cis-acting elements of DNA, usually about from 10 to 300 bp, that act on a promoter to increase its transcription. Enhancers are relatively orientation and position independent, having been found 5' (Laimins et al., *Proc. Natl. Acad. Sci. USA*, 78:993 [1981]) and 3' (Lusky et al., *Mol. Cell Bio.*, 3:1108 [1983]) to the transcription unit, within an intron (Banerji et al., *Cell*, 33:729 [1983]), as well as within the coding sequence itself (Osborne et al., *Mol. Cell Bio.*, 4:1293 [1984]). Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature*, 297:17–18 (1982) on enhancing elements for activation of eukaryotic promoters. The enhancer may be spliced into the vector at a position 5' or 3' to the polypeptide-encoding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the polypeptide of interest.

Particularly useful in the practice of this invention are expression vectors that provide for the transient expression in mammalian cells of DNA encoding the polypeptide of interest. In general, transient expression involves the use of an expression vector that is able to replicate efficiently in a host cell, such that the host cell accumulates many copies of the expression vector and, in turn, synthesizes high levels of a desired polypeptide encoded by the expression vector. Sambrook et al., supra, pp. 16.17–16.22. Transient expression systems, comprising a suitable expression vector and a host cell, allow for the convenient positive identification of polypeptides encoded by cloned DNAs, as well as for the rapid screening of such polypeptides for desired biological or physiological properties.

Other methods, vectors, and host cells 'suitable for adaptation to the synthesis of the polypeptide of interest in recombinant vertebrate cell culture are described in Gething et al., *Nature*, 293:620–625 (1981); Mantei et al., *Nature*, 281:40–46 (1979); Levinson et al.; EP 117,060; and EP 117,058. A particularly useful plasmid for mammalian cell culture expression of the polypeptide is pRK5 (EP pub. no. 307,247) or pSVI6B (PCT pub. no. WO 91/08291 published Jun. 13, 1991).

Host cells are transformed with the above-described expression or cloning vectors of this invention and cultured in nutrient media modified as appropriate for inducing promoters, selecting transformants, or amplifying the genes encoding the desired sequences. For mammalian cells, the calcium phosphate precipitation method of Graham and van der Eb, *Virology*, 52:456–457 (1978) is preferred. General aspects of mammalian cell host system transformations have been described by Axel in U.S. Pat. No. 4,399,216 issued Aug. 16, 1983. For various techniques for transforming mammalian cells, see Keown et al., *Methods in Enzymology* (1989), Keown et al., *Methods in Enzymology*, 185:527–537 (1990), and Mansour et al., *Nature*, 336:348–352 (1988).

The invention also encompasses hybridomas which secrete monoclonal antibodies in cell culture. Monoclonal antibodies are prepared by recovering immune cells (typically spleen cells or lymphocytes from lymph node tissue) from immunized animals and immortalizing the cells in conventional fashion, e.g., by fusion with myeloma cells or by Epstein-Barr (EB)-virus transformation and screening for clones expressing the desired antibody. The hybridoma technique described originally by Kohler and Milstein, *Eur. J. Immunol.*, 6:511 (1976), and also described by Hammerling et al., In: *Monoclonal Antibodies and T-Cell Hybridomas*, Elsevier, N.Y., pp. 563–681 (1981) has been widely applied to produce hybrid cell lines that secrete high levels of monoclonal antibodies against many specific antigens.

3. Polypeptide Production Phase

The cell growth phase is generally followed by a polypeptide production phase, which is distinct therefrom. In the preferred embodiment, the production phase is carried out in a different culturing vessel from the cell growth phase. However, the same vessel can be employed for each step. For example, it is possible to supply the culture medium of the growth phase with high-osmolality, low-glucose containing medium for production. Alternatively, medium-exchange using cell-fluid separation devices available in the art (e.g., cross-flow filtration, rotating screens or fluidized bed microcarriers) enables the same vessel to be used.

The production phase involves inoculating the cultured animal cells of the growth phase at a cell seed density of at least about $1.0 \times 10^6$ cells/mL, preferably at least about $3.0 \times 10^6$ cells/mL. The animal cells are cultured at a starting osmolality of about 400–600 mOsm, more preferably 400–500 mOsm, in a culturing vessel such as that exemplified for the growth phase.

In order to achieve a culture medium having the osmolality specified, the PS-04, Diesel or Super cell culture media disclosed above can be used, and the osmolality of the culture medium can be increased via the addition of the basal concentration of glucose and a salt (such as NaCl, for example). This type of culture medium contains an excess of amino acids in order to provide additional cell nutrients and achieve a high starting osmolality. However, as will be readily apparent to the ordinarily skilled practitioner, the concentration(s) of other constituents in the culture medium can be adjusted in order to reach the desired osmolality.

Preferably, the osmolality is maintained at substantially the desirable range throughout the culturing. Conveniently, controlling the supply of glucose to the cell culture medium helps to prevent excessive increases in osmolality substantially above the desirable optimum.

Accordingly, the production phase is carried out in the presence of a concentration of glucose controlled; throughout the culturing to be within a range between about 0.01 and 1 g/L, preferably 0.02–0.5 g/L, and more preferably 0.05–0.2 g/L. In order to monitor and control the glucose concentration of the culture medium in the range specified, FIA or other automated on-line control systems are useful.

Preferably, the glutamine concentration is also controlled throughout the culturing to be in a range of 0.2 to 2 mM, more preferably 0.5 to 1 mM. Control of the glutamine concentration can be achieved using a FIA system similar to that discussed above, for example.

The culture conditions, such as temperature, pH, $dO_2$ and the like, are those previously used with the host cell selected for protein production, and will be apparent to the ordinarily skilled artisan. For example, the pH may be adjusted to a range between 6.5 and 7.5 and the temperature for production may be between 30 and 38° C.

An advantageous feature of the above invention is that the production cycle can be reduced from the normal time of about 10–15 days or more for recombinant proteins to about 9 days or less, preferably 7 days or less. In certain embodiments (e.g., where the polypeptide of interest is DNase) the production phase is terminated before the maximum polypeptide titer is obtained. This is advantageous as the resultant DNase composition has a reduced percentage deamidation compared to DNase produced in longer runs.

Following the polypeptide production phase, the polypeptide of interest is recovered from the culture medium using techniques which are well established in the art.

4. Polypeptide Purification

The polypeptide of interest preferably is recovered from the culture medium as a secreted polypeptide, although it also may be recovered from host cell lysates when directly expressed without a secretory signal.

As a first step, the culture medium or lysate is centrifuged to remove particulate cell debris. The polypeptide thereafter is purified from contaminant soluble proteins and polypeptides, with the following procedures being exemplary of suitable purification procedures: by fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; and protein A Sepharose columns to remove contaminants such as IgG. A protease inhibitor such as phenyl methyl sulfonyl fluoride (PMSF) also may be useful to inhibit proteolytic degradation during purification. One skilled in the art will appreciate that purification methods suitable for the polypeptide of interest may require modification to account for changes in the character of the polypeptide upon expression in recombinant cell culture.

The following examples are offered by way of illustration and not by way of limitation. The disclosures of all literature references cited in the specification are expressly incorporated herein by reference.

EXAMPLE 1

Cell Growth and Productivity vs Osmolality

The impact of osmolality on cell growth and productivity was determined in petri dish culture. CHO cells were transformed with nucleic acid encoding recombinant human deoxyribonuclease (rhDNase) using the techniques disclosed by Shak et al., PNAS, 87: 9188–9192 (1990), expressly incorporated by reference herein. These recombinant CHO cells were grown in petri dish culture in medium consisting essentially of the Super medium referred to in U.S. Pat. No. 5,122,469 (except that NaCl was added to the Super medium at various concentrations in order to achieve an osmolality in the range from about 260–680 mOsm). The glucose concentration was 4.5 g/L. The osmolality was measured using an OSMETTE™ osmometer. The pH of the culture medium was 7.2 and cells were cultured in a 37° C. humidified $CO_2$ incubator. The results are depicted in FIG. 2; the closed circles represent the CHO cell density (expressed as $10^5$ cells/ml) after 5 days and the open circles represent the relative DNase concentration after 8 days.

EXAMPLE 2

Osmolality Change vs Glucose Concentration

The osmolality change during cultivation at various controlled glucose concentrations versus high (batch) glucose concentration was quantified. CHO cells transformed with rhDNase cells (see Shak et al., supra) were cultured in a pH controlled Applikon (Foster City, Calif.) bioreactor at a 2.5 liter working volume. The Super cell culture medium of U.S. Pat. No. 5,122,469 (with adjusted NaCl and glucose concentrations) was used and the CHO cells were stirred at 150 rpm agitation. The initial osmolality was adjusted to about 270–300 mOsm via the amount of NaCl added. The cell seed density was $1 \times 10^6$ cells/ml. The other cell culture medium and culturing conditions were: pH=7.2, $dO_2$=60% and culturing temperature=37° C. Glucose was added either in batch (at a concentration of 12 g/L) at the start of the culturing or was controlled throughout the culturing to be at a concentration of 0.05 g/L, 0.2 g/L or 0.5 g/L, respectively. Glucose control was achieved using FIA and the osmolality of the medium was measured using an OSMETTE™ osmometer. The effects of glucose concentration and glucose control on osmolality are depicted in FIG. 3.

EXAMPLE 3

Cell Growth vs Glucose Concentration

The effects of glucose concentration and glucose control on growth of CHO cells transformed with TBFβ were investigated. CHO cells were transformed with TGFβ using the techniques disclosed in Brunner et al., Mol. Endocrinol., 6(10): 1691–1700 (1992). The results are depicted in FIG. 4; the ▣ symbols represent the experiment wherein on line glucose control (OLGC) at 0.1 g/L using FIA was performed throughout the culturing, the ♦ symbols represent the experiment wherein the glucose was added initially in batch (8 g/L). In the experiments, CHO cells were cultured in an Applikon bioreactor at a 2.5 liter working volume. Super cell culture medium (with adjusted NaCl and glucose concentrations) was used and the CHO cells were stirred at 150 rpm agitation. The initial osmolality was adjusted to 280 mOsm via the addition of NaCl. The osmolality of the medium was measured using an OSMETTE™ osmometer. The cell seed density was $8 \times 10^5$ cells/ml. The other cell culture medium and culturing conditions were: pH=7.2, $dO_2$=60% and culturing temperature=37° C.

EXAMPLE 4

Productivity and Run Time vs Glucose Concentration

FIG. 5 depicts the results of the following experiment wherein the effect of controlling glucose concentration (via OLGC using FIA) versus adding a high (batch) glucose concentration at the start of the culturing, on the final concentration of rhDNase produced in recombinant cell culture. The relative concentration of DNase produced by recombinant CHO cells is given. The glucose control set point was 0.5 g/L in the OLGC experiment and the starting glucose concentration in the batch experiment was 12 g/L. A high starting osmolality (460 mOsm/kg; adjusted using NaCl) and cell seed density ($3.5 \times 10^6$ cells/ml) were used. CHO cells were cultured in an Applikon bioreactor at a 2.5 liter working volume. Super cell culture medium was used and the CHO cells were stirred at 150 rpm agitation. The other cell culture medium and culturing conditions were: pH=7.2, $dO_2$=60% and culturing temperature=37° C.

It was shown that, by controlling glucose, 29% more product could be recovered in 12 days of culturing or an overall reduction in the production run time by 18% at similar product concentration could be achieved.

In a similar experiment (under the same conditions discussed above), glucose control was further shown to be desirable insofar as it lead to a reduction in the extent of deamidation of DNase both directly and as a consequence of enabling the production run times to be reduced. The extent of DNase deamidation where glucose was added in batch or controlled at 0.5 g/L, is shown in the following Table 5. The DNase samples from day 9 and day 12 were analyzed for deamidation.

TABLE 5

DNase Deamidation vs Time in Culture

| | Batch Glucose | | Controlled Glucose | |
|---|---|---|---|---|
| Day | DNase Conc (mg/L) | % Deamidation | DNase Conc (mg/L) | % Deamidation |
| 9 | 740 | 47 | 804 | 43 |
| 12 | 815 | 67 | 878 | 56 |

EXAMPLE 5

TGFβ Production

The impact of OLGC, compared to batch addition of glucose, on production of TGFβ by recombinant CHO cells was evaluated. CHO cells were transformed with nucleic acid encoding TGFβ using the techniques of Brunner et al., supra. These recombinant CHO cells were grown in an Applikon bioreactor supplied with the Super medium referred to in U.S. Pat. No. 5,122,469 (with adjusted NaCl and glucose concentrations). The starting osmolality was adjusted to 450 mOsm using NaCl. The cell seed density was $3.5 \times 10^6$ cells/ml. The other cell culture medium and culturing conditions were: pH 7.2, $dO_2$=60% and culturing temperature=37° C. The results are depicted in FIG. 6; one curve represents TGFβ production where the CHO cells were cultured using OLGC with the glucose concentration set at 0.1 g/L and the other curve represents TGFβ production with a batch addition of glucose at 8 g/L. Glucose control facilitated a reduction in the production time by about 40%.

We claim:

1. A method of growing animal cells in fed batch cell culture comprising culturing the cells:

at a starting osmolality of about 280–330 mOsm;

in the presence of glucose controlled throughout the culturing to be at a concentration between about 0.02 and 1.0 g/L, inclusive, by adding glucose to the cell culture as required to maintain said glucose concentration and thereby controlling osmolality of the cell culture; and in the presence of glutamine controlled throughout the culturing to be at a selected glutamine concentration by adding glutamine to the cell culture as required to maintain said glutamine concentration.

2. The method of claim 1 wherein the glutamine concentration is between about 0.2 and about 2 mM.

3. The method of claim 2 wherein the glutamine concentration is between about 0.5 and about 1 mM.

4. The method of claim 1 wherein the glucose concentration is between about 0.2 and about 0.5 g/L.

5. The method of claim 4 wherein the glucose concentration is between about 0.02 and about 0.2 g/L.

6. The method of claim 1 wherein the culture medium contains excess amino acids.

7. The method of claim 1 wherein the initial cell seed density is between about $3 \times 10^5$ and about $1.5 \times 10^6$ cells/mL.

8. The method of claim 1 wherein the cells are mammalian cells.

9. The method of claim 8 wherein the cells are Chinese Hamster Ovary (CHO) cells.

10. The method of claim 8 wherein the mammalian cells comprise a nucleic acid encoding a polypeptide.

11. The method of claim 1 wherein the glucose control comprises flow injection analysis (FIA).

* * * * *